United States Patent [19]

Young

[11] 4,423,724
[45] Jan. 3, 1984

[54] INHALATION DEVICE FOR POWDERED MEDICAMENTS

[75] Inventor: David M. Young, Loughborough, England

[73] Assignee: Fisons Limited, England

[21] Appl. No.: 270,237

[22] Filed: Jun. 4, 1981

[30] Foreign Application Priority Data

Jun. 6, 1980 [GB] United Kingdom ................ 8018586

[51] Int. Cl.³ .......................................... A61M 15/00
[52] U.S. Cl. ......................... 128/203.15; 128/203.21; 604/58
[58] Field of Search .......................... 128/203.15, 266; 221/87, 88, 89; 604/58

[56] References Cited

U.S. PATENT DOCUMENTS 3,807,400  4/1974  Cocozza ........................ 128/203.15
3,918,451  11/1975  Steil .............................. 128/203.15
4,116,195  9/1978  James ............................ 128/203.15
4,249,526  2/1981  Dean et al. .................... 128/203.15

Primary Examiner—Henry J. Recla
Assistant Examiner—Karin M. Reichle
Attorney, Agent, or Firm—Merriam, Marshall & Bicknell

[57] ABSTRACT

An inhalation device for a powdered medicament contained initially in a container, which device comprises a swirl chamber adapted to receive a medicament container and having air inlets thereinto and a mouthpiece in communication therewith; a container receiving cavity also in communication with said swirl chamber; and piercing means operable to pierce a medicament container when in the cavity and to withdraw from the pierced container, said cavity being provided with obstructive means to prevent the container re-entering the cavity after being pierced.

9 Claims, 6 Drawing Figures

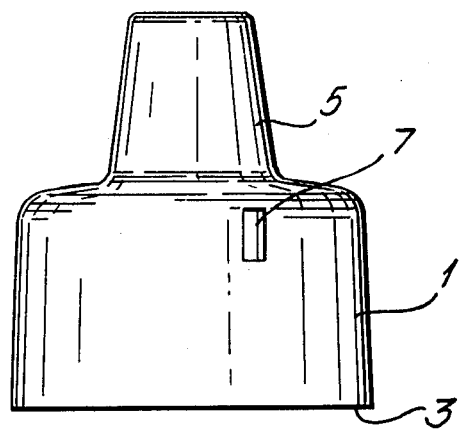
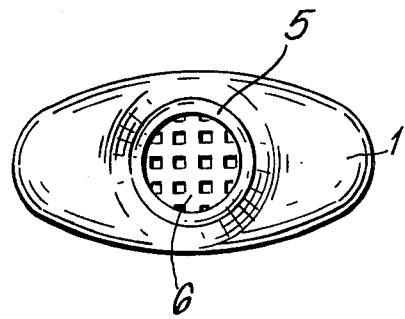
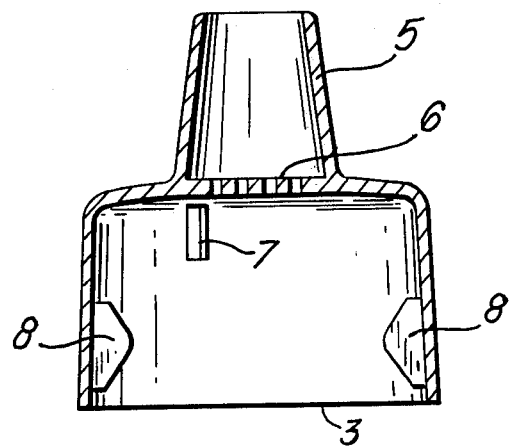

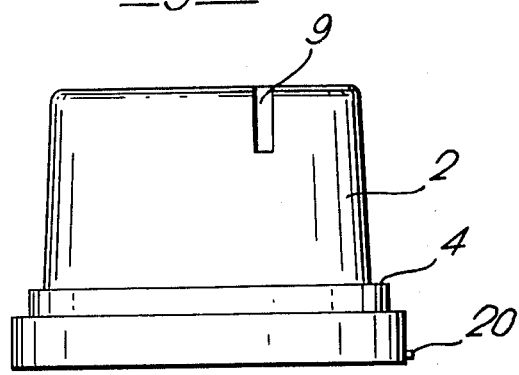
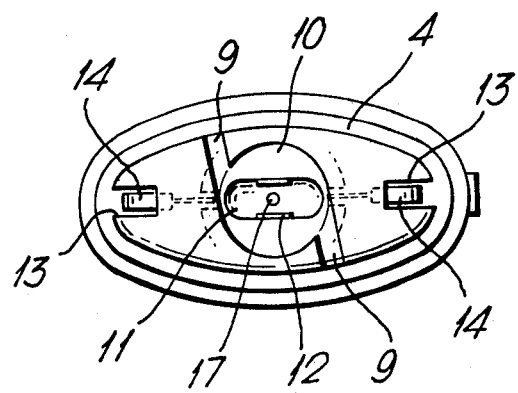
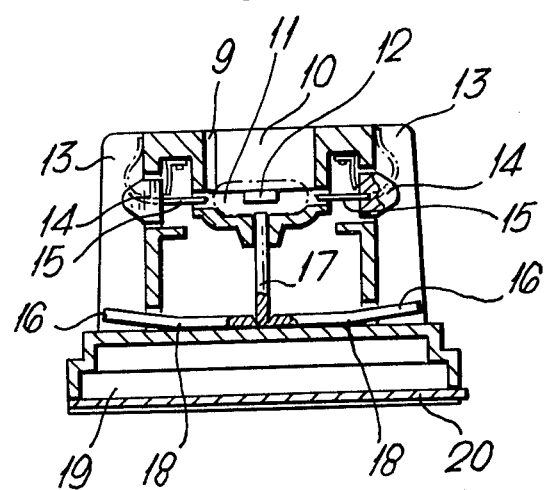

INHALATION DEVICE FOR POWDERED MEDICAMENTS

This invention concerns improvements in or relating to inhalation devices for powdered medicaments.

Many inhalation devices are known in which a medicament powder contained initially in a container, e.g. a gelatin capsule, is administered to the patient by first opening the container and then entraining the powder in an airstream which is inhaled.

The opening of the container and the subsequent entrainment of the powder can be achieved in a variety of ways. However, in some types of devices, e.g. that of U.K. Patent Specification No. 1,485,163, the container is first placed in a cavity or recess in the device and is pierced therein by pins which are then retracted. On inhalation through such a device, the pierced container is dislodged from the cavity into a swirl chamber having tangential air inlets, and the flow of air therethrough causes the container to spin and thus expel the powder through the pierced holes. The medicament entrained in the air stream is then inhaled via the mouth or nose by the user.

In most cases, the medicament container comprises a hard gelatin capsule. Such capsules require quite large forces to pierce holes of sufficient diameter to allow satisfactory expulsion of medicament. It therefore follows that the cavity in which the capsule is pierced must hold it as firmly as possible, otherwise it may tend to move rather than be pierced. However, the more firmly the cavity holds the capsule during the piercing operation, the more difficult it is to dislodge the capsule therefrom. Consequently, in many cases, it is found that the capsule tends to remain in the cavity after piercing, and little or none of the medicament is inhaled since the capsule does not enter the swirl chamber.

In practice hitherto, a compromise solution has been adopted in which a deep cavity is provided which effectively allows the capsule freedom to move in only one direction, i.e. out of the cavity. Piercing can be satisfactorily achieved provided that gravity initially acts to hold the capsule in the cavity, and that the piercing pins do not cause the capsule to rise up in the cavity rather than be pierced. Thereafter, expulsion of the powder from the capsule can be achieved provided that the capsule is first shaken out of the cavity and does not fall back into it. However, the capsule frequently does re-enter the cavity with consequent loss of function of the device.

This invention seeks to provide an inhalation device which reduces or minimizes these drawbacks.

Accordingly, in one aspect, this invention provides an inhalation device for a powdered medicament contained initially in a container, which derive comprises a swirl chamber adapted to receive a medicament container and having air inlets thereinto and a mouthpiece in communication therewith; a container receiving cavity also in communication with said swirl chamber; and piercing means operable to pierce a medicament container when in the cavity and to withdraw from the pierced container, said cavity being provided with obstructive means to prevent the container re-entering the cavity after being pierced.

The means to prevent the container re-entering the cavity after being pierced preferably takes the form of a mechanism which acts to introduce an obstruction into the cavity. For example, it may take the form of a member which is moveable into said cavity after piercing which provides a physical impediment to the re-entry of the capsule. Conveniently, such a member is moveable so as also to eject the capsule from the cavity.

In a preferred embodiment, the member is moved into the cavity immediately after the capsule has been pierced, by a continuation of the action necessary to pierce the capsule. Thus, if piercing is effected by a cam surface being caused to move over spring biassed piercing pins, further movement of the cam surface in the same direction desirably causes the member to move into the cavity to eject the capsule and prevent its re-entry. Thus, for example a pin can be reciprocated by means of one or more rocker bars, e.g. pivoted bars or bars having a fulcrum formed thereon, one end of which is linked to or engages the pin, the other end being engaged by the cam actuating mechanism. As the cam actuating mechanism bears against the end of the rocker bar it causes the bar to move about its fulcrum and move the pin. If desired means, e.g. a spring, can be provided to retract the pin when the cam actuating mechanism is withdrawn.

Other means to prevent the container re-entering the cavity after being pierced can also be employed. Thus, the means may take the form of a constriction at or near the top of the cavity, past which the capsule must be pushed to enter the cavity. With such a construction, an ejector mechanism should be provided to eject the capsule past the constriction and into the swirl chamber after being pierced. Such an ejector mechanism need not however remain in position to prevent re-entry of the capsule as this is provided by the constriction itself.

The constriction, if arranged appropriately, may also provide a further benefit. Thus, if it extends sufficiently into the cavity that it still bears on the capsule when the capsule is fully in the cavity it may serve to hold the capsule firmly enough during piercing to prevent it riding up and giving either no piercing or piercing in undesired locations.

The invention will now be described by way of illustration only, with reference to a preferred form thereof shown in the accompanying drawings, in which:

FIG. 1 is an elevational view of the mouthpiece portion of a device according to the invention;

FIG. 2 is a top plan view of the mouthpiece portion of the device of FIG. 1;

FIG. 3 is a vertical cross-section through the mouthpiece portion shown in FIGS. 1 and 2;

FIG. 4 is an elevational view of the body portion of the inhaler of FIGS. 1 to 3;

FIG. 5 is a top plan view of the body portion of FIG. 4; and

FIG. 6 is a vertical cross-section through the body portion of FIGS. 4 and 5.

Similar features in each drawing are denoted by the same reference numeral.

The mouthpiece portion 1 shown in FIG. 1 and the body portion 2 shown in FIG. 4 are of co-operating cross-section, e.g. elliptical as shown, and are adapted in use to be assembled so that the mouthpiece portion fits over and around the body portion, preferably so that bottom edge 3 of the mouthpiece portion rests on ledge 4 of the body portion. The two portions are separable to enable a capsule of medicament (shown in dotted outline in FIG. 6) to be inserted into and removed from a chamber within the device.

The mouthpiece portion 1 is generally hollow and has a narrow diameter portion 5 which acts as the discharge outlet. Preferably, it also has a grating 6, the function of which is to retain the capsule and prevent it or large fragments of it being inhaled through the outlet 5. Passageways 7 are provided through the wall of the mouthpiece portion which are to discharge air through co-operating passages 9 in the base member into a generally circular chamber within the base member. Also provided within the mouthpiece portion 1 are two rigid cam actuating projections 8.

In the body portion 2 shown in FIGS. 4–6 there are provided two air inlet passageways 9 which lead into a swirl chamber 10. Preferably swirl chamber 10 is of substantially circular cross section and is located generally co-axially with the longitudinal axis of the device. The passageways 9 register with the passageways 7 when the mouthpiece portion and the body portion are assembled and are so designed that they induce a swirling air flow within the chamber 10 when air is sucked through the device via outlet 5. It is preferred that passageways 9 lead tangentially into chamber 10. Within the base of the swirl chamber 10 there is provided a capsule-receiving cavity 11 which closely approximates to the shape of the capsule. Cavity 11 is preferably provided with projections 12 which serve to hold the capsule firmly therein.

The body portion 2 is provided with one or more, e.g. two as shown, piercing members, e.g. needles 15, which are to pierce a capsule held in cavity 11. The needles can be sharpened to a conventional conical tip or, more preferably, are formed with a cutting face formed across the tip of the needle at an angle to the axis of the needle. The needle 15 is provided at the non-operative end thereof with a member co-operating with the projections 8 within the mouthpiece portion 2 to form therewith a camming surface. Preferably needle 15 is spring biased away from cavity 11 so that a capsule is free to move in and out of the cavity. Alternatively, the needle can be formed on the end of a spring arm (shown dotted in FIG. 6) which is engaged by the projections 8 within the mouthpiece portion 1. Preferably, the needle 15 is provided with a head 14 and both the heads 14 and the projections 8 are formed with co-operating cammed or inclined faces as shown in the drawings which engage with one-another as the mouthpiece portion 1 is fitted onto the body portion 2 to cause the needle to be reciprocated to pierce a capsule in cavity 11 and withdraw. Conveniently, body portion 2 is formed with longitudinal guide grooves 13 adapted to receive projections 8, and heads 14 are located in these grooves.

Body portion 2 is provided with means for ejecting a pierced capsule from the cavity 11. This means takes the form of one, or preferably two as shown, cranked arms 16 one end of which projects into groove 13 to engage with projection 8 or the base of the mouthpiece portion 1 when portion 1 is pushed fully home on portion 2. The other end of arm 16 engages with a longitudinal pin 17 which is reciprocatable within a bore in portion 2 from an inoperative position to an operative position in which it extends into cavity 11 to eject a capsule from the cavity. The pin remains in its operative position until the mouthpiece portion 1 is withdrawn from body portion 2 and releases the ends of the cranked arms. Cranked arms 16 act as rocker arms and pivot about the fulcrum formed at the elbow of their crank. However, arms 16 could be formed as straight bars having a ridge, spot or other form of projection on their underside to provide the fulcrum. Alternatively, arms 16 could be pivotally mounted in body portion 2, e.g. by a pin pressing through portion 2 and the arm.

The arms 16 bear against pin 17 or can be formed integrally therewith, e.g. as a single moulding in plastics having hinge lines formed therein as shown in FIG. 6. Alternatively, arms 16 can be pivotally linked to the base of pin 17. If desired pin 17 and/or arms 16 can be spring biased to retract pin 17 from cavity 11 when arms 16 are released.

In operation of the device, portion 1 is removed from body portion 2 to expose chamber 10 and cavity 11. A capsule is inserted into cavity 11 and pushed home to be held firmly by projections 12. Pin 17 is in its non-operative retracted position with the free ends of arms 16 raised as shown in FIG. 6. Needles 15 are retracted with heads 14 projecting into groove 13.

Mouthpiece portion 1 is then mounted on body portion 2 with projections 8 engaging in groove 13 and is pushed home. As it is pushed home the projections 8 engage the heads 14. This action first forces each of the heads 14 and their needles 15 inwardly to pierce the ends of a capsule placed in the cavity, and then, on further movement, allows both needles 15 to withdraw under their spring bias from the capsule.

On yet further movement, after the heads 14 have ridden over cam projections 8, the projections then engage the free ends of cranked arms 16. The arms 16 are forced downwardly by the cam projections 8, and are caused to rotate about their elbows 18, thereby causing pin 17 to project into the cavity 11 and bear on the capsule to eject it from the cavity past the projections 12. The pin 17 remains in its extended position and prevents the capsule re-entering the cavity 11.

The patient then inhales through the outlet 5, e.g. by inserting it into his nostril or mouth. Air is drawn into the swirl chamber 10 through passageways 7 and tangential passageways 9 thereby creating a vortex in the swirl chamber in which the capsule is rotated. The medicament powder contained in the capsule is expelled and is entrained in the air stream to pass through the grating 6 and be inhaled.

The mouthpiece portion 1 is then removed, the old capsule is removed, and if desired a new capule is placed in the cavity 11.

As a further feature, there is provided a hollow container portion 19 in the body portion 2 for the storage of several capsules of medicament. Access to said container portion 19 is achieved by a flip-type cover portion 20.

Whilst the invention has been described above in terms of the relative longitudinal reciprocation of portions 1 and 2, it will be appreciated that portions 1 and 2 could be formed so that relative rotation of the two portions caused actuation of the piercing and ejection operations.

I claim:
1. An inhalation device for supplying to a user a powdered medicament contained initially in a container; which device comprises: a housing wherein is situated a swirl chamber adapted to receive a medicament container and having air inlets thereinto and a mouthpiece in flow communication therewith such that the medicament can pass from the swirl chamber through the mouthpiece to the user; a container receiving cavity within said housing also in communication with said swirl chamber; and piercing means movably operable to pierce a medicament container when in the cavity and to withdraw from the pierced container, said cavity being provided with means to transfer the container from the cavity to the swirl chamber, said transfer means actuatable to prevent the container from re-entering the cavity after being transferred; actuating means for actuating said piercing means and said transfer means, said transfer means being actuated by a continuation of the movement in the same direction of said actuating means subsequent to actuating the piercing means.

2. An inhalation device for supplying to a user a powdered medicament contained initially in a container, which device comprises: a housing wherein is situated a swirl chamber adapted to receive a medicament container and having air inlets thereinto and a mouthpiece in flow communication therewith such that the medicament can pass from the swirl chamber through the mouthpiece to the user; a container receiving cavity within said housing also in communication with said swirl chamber; and piercing means movably operable to pierce a medicament container when in the cavity and to withdraw from the pierced container, said cavity being provided with actuatable transfer and obstructive means to (a) transfer the container from the cavity to the swirl chamber, and (b) prevent the container from re-entering the cavity after being transferred, said actuatable transfer and obstructive means including an opening in said housing into said cavity, a pin member slidably mounted in said opening, a lever mechanism pivotably connected to said housing and said pin member whereby said pin member is introduced into the cavity by movement of said associated lever mechanism mounted on said housing adjacent said cavity.

3. A device as claimed in claim 2 wherein the pin member is reciprocatably moved by said lever mechanism to ejectably transfer the medicament container from the cavity into the swirl chamber.

4. A device as claimed in claim 3 wherein the cavity is also provided with one or more projections adapted to grip said container when in the cavity and to impede re-entry of the container into the cavity once it is ejected.

5. A device as claimed in claim 2, wherein the transfer and obstructive means are actuated by a continuation of the movement operatively actuating the piercing means.

6. A device as claimed in claim 2 wherein the device is formed by two cooperating, mating sections, comprising respectively said housing and said mouthpiece relatively movable with respect to each other; one section including projections and the other section including said piercing means and said transfer and obstructive means; said projections adapted to actuate by a camming operation the piercing means and the transfer and obstructive means during movable mating of said sections.

7. A device as claimed in claim 2 wherein said lever mechanism includes a lever arm pivotable about a fulcrum for reciprocatable moving said pin member into and out of said cavity.

8. A device as claimed in claim 7 wherein the lever arm includes a crank arm having an elbow, said crank arm adapted to operatively pivot about its elbow in response to a continuation of the movement operatively actuating the piercing means.

9. An inhalation device comprising a body portion end a hollow mouthpiece portion having an open end into which is located said body portion, the mouthpiece and body portions being longitudinally relatively movable with respect to one another; the body portion comprising a housing within which is situated an internal chamber adapted to receive a medicament container and having a container piercing cavity in communication with the chamber such that the container can pass from the cavity to the chamber; the mouthpiece portion having an outlet communicating with the chamber such that the medicament from within the container can pass from the chamber through the mouthpiece to the user and both portions being provided with cooperating passages in tangential communication with the chamber whereby air can be drawn through the device from said passages to the outlet so as to cause a swirling air flow through the chamber; the body portion including a transverse opening leading into said cavity, a spring biassed piercing needle mounted in said body portion such that said needle is movable and reciprocated in said transverse opening into the cavity so as to pierce a container when in the cavity and further including another opening leading into said cavity opposite said chamber, a pin member slidably mounted in said another opening, a lever arm pivotably mounted on said body portion about a fulcrum and acting on said pin member so as to movably reciprocate the pin member into the cavity to eject a container from the cavity into the chamber; the mouthpiece portion having an inwardly directed projection and said needle and lever arm being mounted with respect to said body portion such that said projection, needle and lever arm are in alignment whereby said; projection is adapted to engage in sequence the needle and the lever arm upon insertion of the body portion into the mouthpiece portion so as to cause said reciprocatable movement thereof.

* * * * *